United States Patent
Englert et al.

(10) Patent No.: US 11,060,131 B2
(45) Date of Patent: Jul. 13, 2021

(54) SOLID PHASE NUCLEIC ACID TARGET CAPTURE AND REPLICATION USING STRAND DISPLACING POLYMERASES

(71) Applicant: ALEXA INC., Etobicoke (CA)

(72) Inventors: David Frederick Englert, West Hartford, CT (US); Kelly Kai Yin Seto, Toronto (CA)

(73) Assignee: ANGLE EUROPE LIMITED, Guildford (GB)

( * ) Notice: Subject to any disclaimer, the term of this patent is extended or adjusted under 35 U.S.C. 154(b) by 347 days.

(21) Appl. No.: 15/561,083

(22) PCT Filed: Mar. 29, 2016

(86) PCT No.: PCT/CA2016/050367
§ 371 (c)(1),
(2) Date: Sep. 25, 2017

(87) PCT Pub. No.: WO2016/149837
PCT Pub. Date: Sep. 29, 2016

(65) Prior Publication Data
US 2018/0057855 A1    Mar. 1, 2018

Related U.S. Application Data

(60) Provisional application No. 62/138,191, filed on Mar. 25, 2015.

(51) Int. Cl.
*C12Q 1/68* (2018.01)
*C12Q 1/6806* (2018.01)
(Continued)

(52) U.S. Cl.
CPC ....... *C12Q 1/6806* (2013.01); *C12N 15/1006* (2013.01); *C12N 15/1013* (2013.01);
(Continued)

(58) Field of Classification Search
None
See application file for complete search history.

(56) References Cited

U.S. PATENT DOCUMENTS 5,399,491 A   3/1995  Kacian et al.
5,422,252 A   6/1995  Walker et al.
(Continued)

FOREIGN PATENT DOCUMENTS

WO         0060919 A2      10/2000
WO         WO0060919    *  10/2000   ............... C12Q 1/68
WO         WO-0060919 A2 * 10/2000   ........... C12Q 1/6837

OTHER PUBLICATIONS

Westin et al. (Nature Biotechnology, 2000, vol. 18, p. 199-204) (Year: 2000).*

Elnifro et al., "Multiplex PCR: Optimization and Application in Diagnostic Virology," Clin Microbiol Rev. 13:559, 2000, pp. 559-570.

Shum et al., "Chemically modified primers for improved multiplex PCR," Anal Biochem 388: 266, 2009, pp. 1-15.

(Continued)

*Primary Examiner* — Stephanie K Mummert
(74) *Attorney, Agent, or Firm* — Hill & Schumacher

(57) ABSTRACT

A method and kit for the capture and purification of specific nucleic acids from a sample with affinity capture probes on a solid support and for the replication of said nucleic acids with a strand displacing polymerase, whereby a second primer complementary to a sequence in each of the target nucleic acids distinct from that bound by capture probes is also bound to the nucleic acid targets, and extension of one of the primers on each target effects the separation of the copied nucleic acid strands from the solid support. Incorporation of universal nucleic acid sequences during their replication enables the simultaneous and highly specific amplification of multiple nucleic acid target sequences with minimal production of artifacts.

31 Claims, 7 Drawing Sheets

(51) Int. Cl.
  *C12Q 1/6844* (2018.01)
  *C12N 15/10* (2006.01)
  *C12Q 1/6837* (2018.01)
  *C12Q 1/686* (2018.01)

(52) U.S. Cl.
  CPC .......... *C12Q 1/686* (2013.01); *C12Q 1/6837* (2013.01); *C12Q 1/6844* (2013.01); *C12Q 1/6846* (2013.01)

(56) References Cited

U.S. PATENT DOCUMENTS

| | | | |
|---|---|---|---|
| 5,470,723 A | | 11/1995 | Walker et al. |
| 5,624,825 A | * | 4/1997 | Walker .................. C12Q 1/6853 435/91.2 |
| 5,648,211 A | | 7/1997 | Fraiser et al. |
| 5,759,773 A | | 6/1998 | Tyagi et al. |
| 5,882,856 A | | 3/1999 | Shuber |
| 5,916,779 A | | 6/1999 | Pearson et al. |
| 6,207,372 B1 | | 3/2001 | Shuber |
| 7,579,154 B2 | | 8/2009 | Chun |
| 7,713,697 B2 | | 5/2010 | Becker et al. |
| 7,955,794 B2 | | 6/2011 | Shen et al. |
| 8,124,346 B2 | | 2/2012 | Chun |
| 8,183,359 B2 | | 5/2012 | Becker et al. |
| 8,198,027 B2 | | 6/2012 | Brentano et al. |
| 8,632,977 B2 | | 1/2014 | Chun |
| 2014/0066318 A1 | | 3/2014 | Frisen et al. |
| 2014/0255928 A1 | * | 9/2014 | Belousov ............. C12Q 1/6844 435/6.11 |

OTHER PUBLICATIONS

Pastinen et al., "A System for Specific, High-throughput Genotyping by Allele-specific Primer Extension on Microarrays," Genome Res. 10:1031, 2000, pp. 1031-1042.

Brownie et al., "The elimination of primer-dimer accumulation in PCR," Nucleic Acids Res. 25:3235, 1997, pp. 3235-3241.

Tyagi et al., "Extremely sensitive, background-free gene detection using binary probes and QB replicase," Proc Natl Acad Sci 9: 5395, 1996, pp. 5395-5400.

Hsuih et al., "Novel, Ligation-Dependent PCR Assay for Detection of Hepatitis C Virus in Serum," J Clin Microbiol. 34, 501, 1996, pp. 501-507.

Fan et al., "A Versatile Assay for High-Throughput Gene Expression Profiling on Universal Array Matrices," Genome Res. 14:878, 2004, pp. 878-885.

Fan et al., "Highly Parallel SNP Genotyping," Cold Spring Harb Symp Quant Biol. 68:69, 2003, pp. 69-78.

Kievits et al., "NASBA isothermal enzymatic in vitro nucleic acid amplification optimized for the diagnosis of HIV-1 infection," J Virol Methods 35:273, 1991, pp. 273-286.

"Whole-Genome Gene Expression DASL Assay Guide," Illumina Proprietary, Catalog # DA-800-1002, Part #11322443 Rev. B; Illumina, Inc.; 2008-2010, pp. 1-115.

Han et al. "Simultaneous Amplification and Identification of 25 Human Papillomavirus Types with Templex Technology," J Clin Microbiol. 44:4157, 2008, pp. 4157-4162.

International Search Report, International Application No. PCT/CA2016/050367, dated Aug. 8, 2016.

\* cited by examiner

SOLID PHASE NUCLEIC ACID TARGET CAPTURE AND REPLICATION USING STRAND DISPLACING POLYMERASES

FIELD

The present disclosure relates to methods required for nucleic acid tests to qualitatively and/or quantitatively detect multiple nucleic acid target sequences in biological samples. The nucleic acid target sequences are often present in very small quantities in large backgrounds of unrelated nucleic acid sequences, and reliable detection requires extensive and highly specific amplification. The methods of the present disclosure provide for the attachment of universal priming sequences to target sequences in processes using strand displacing polymerases to effect strand separation under mild conditions. These methods are amenable to automation with relatively simple devices.

BACKGROUND

Most methods for nucleic acid analysis offer limited multiplexing capabilities—e.g., standard multiplex polymerase chain reaction (PCR) methods are limited to a few different targets due to interactions between complex mixtures of primers at high concentrations. Although multiplex PCR is commonly used to amplify multiple targets from the same sample, careful optimization is required due to the potential of non-specific amplifications, preferential target amplification and primer-dimer artifacts. Primer-dimer artifacts are efficiently amplified and not only lower the specificity of the amplification but consume PCR reagents and lower amplicon yield (Elnifro et al., Clin Microbiol Rev. 13:559, 2000; Shum and Paul, Anal Biochem 388: 266, 2009). For example, in a genotyping assay six separate PCR reactions with selected pools of primer pairs were required to amplify thirty-one different genetic loci (Pastinen et al., *Genome Res.* 10:1031, 2000).

The consistency of multiplex PCR reactions have been improved and the deleterious effects of primer-dimers have been minimized by the use of universal primers for amplification.

U.S. Pat. Nos. 5,422,252, 5,470,723 and 5,648,211 have disclosed methods whereby universal sequences may be appended to multiple target sequences with target-specific adapter primers so that amplification can be performed with a single pair of primers in an isothermal method called strand displacement amplification (SDA). Primer-dimer artifacts produced by multiple pairs of target-specific adapter primers were minimized by using them at substantially lower concentrations than the universal amplification primers.

U.S. Pat. Nos. 5,882,856 and 6,207,372 have disclosed the use of universal primers for multiplex amplification that avoided preferential target amplification in single polymerase chain reactions (PCR) under standard conditions that do not have to be optimized for each target. More uniform amplification of target sequences was demonstrated with the use of universal primers.

Whereas the use of universal primers tends to reduce the formation of primer-dimers by target-specific primers, the amplification of primer-dimers which inevitably form in the initial phases of PCR have been minimized by using a single primer sequence on both strands of the amplicons (Brownie et al., Nucleic Acids Res. 25:3235, 1997). Hybrids formed between the ends of small primer-dimer molecules form panhandle structures which result in the relative suppression of their amplification since the formation of panhandles competes with the annealing of PCR primers.

U.S. Pat. No. 5,759,773 disclosed a method whereby complexes consisting of a nucleic acid target, capture probes and binary detection probes could be efficiently isolated on a solid support. See also Tyagi et al., *Proc Natl Acad Sci* 9: 5395, 1996 and Hsuih et al., *J Clin Microbiol.* 34, 501, 1996. After washing the solid support, the complexes of the target and the binary detection probes were dissociated from the solid support for subsequent ligation amplification by enzymatic digestion of the capture probes with RNase H. This method requires that the capture probes consist of RNA/DNA hybrid sequences that will be efficiently digested by the enzyme, and hence lacks general utility for different types of target molecules and capture sequences. Furthermore, only a single target was detected with the method.

U.S. Pat. No. 7,955,794 disclosed a method similar to that in U.S. Pat. No. 5,759,773 in that target molecules were captured on a solid support and complexed with binary detection probes, followed by ligation of the binary probes and amplification of the ligated probes with PCR. This method has been shown to be suitable for the multiplex amplification of a very large number (many thousands) of target sequences in a single reaction. See Fan et al. Genome Res. 14:878, 2004 and Fan et al., Cold Spring Harb Symp Quant Biol. 68:69, 2003. The success of the method depends on the hybridization of the large number of binary detection probes (each containing universal primer sequences) to the target molecules on a solid support, and washing away the excess detection probes before ligation and amplification with universal primers. This effectively removes the large number of unbound oligonucleotide probes with universal primer sequences which would otherwise produce large quantities of primer-dimer artifacts in a polymerase reaction.

Although the above method overcomes a significant limitation in the reliable and efficient amplification of large numbers of target sequences, the process is not amenable to automation in a simple, compact device that would be suitable for routine use in clinical analysis. It requires the use of two separate types of solid support and a denaturation step at 95 degrees C. to recover the products from the second solid support for subsequent amplification. The nucleic must be purified on one type of solid support and then copied and tagged with a ligand in an enzymatic reaction. The tagged nucleic acid is then hybridized to the oligonucleotide pool and captured on a second type of solid support. After washing, two enzymatic reactions are performed on the solid support. After washing the solid support the ligated binary probes are eluted from the solid support by denaturation at 95 degrees C. for PCR amplification.

Nucleic acid targets that have been copied with the incorporation of universal priming sequences may be amplified with a few different amplification methods in which multiple targets can be amplified with universal primers. These methods include strand displacement amplification of SDA (U.S. Pat. No. 5,422,252), Transcription-Mediated Amplification or TMA (U.S. Pat. No. 5,399,491) and Nucleic Acid Sequence Based Amplification or NASBA (Kievits et al., J Virol Methods 35:273, 1991).

These methods require the introduction of primer and/or promoter sequences at both ends of the sequences of interest in the target nucleic acids for subsequent amplification, and this requires the generation of double stranded copies of the target sequences. Different strategies have been used to prime the synthesis of DNA copies with primers having the 5' tail sequences required for amplification.

The SDA method (U.S. Pat. No. 5,422,252) utilizes strand displacement primers to create single-stranded copies of the original nucleic acid target to which other primers can hybridize to produce double-stranded copies with the adapter sequences at each end required for amplification. Subsequent amplification relies on a restriction enzyme to create a nick in a double-stranded DNA molecule from which the DNA target is copied by DNA polymerase.

The TMA method of amplification (U.S. Pat. No. 5,399,491) has been used to amplify RNA target sequences, and relies on the activity of RNase H to digest the original RNA target after reverse transcription to create a single-stranded region the DNA copy for hybridization of a primer in order to generate the double stranded DNA required for transcription. Because of this dependence on RNase H to generate a double stranded copy of the RNA target, the original TMA method is unsuitable for DNA targets. U.S. Pat. Nos. 7,713,697 and 8,183,359 disclosed a method for adapting TMA to DNA targets that utilizes a displacer oligonucleotide to provide a single stranded copy of the DNA that could in turn be copied from a different priming sequence to create a double stranded DNA that includes the double stranded promoter sequence required for TMA amplification.

U.S. Pat. No. 8,198,027 disclosed a method for the capture of an RNA target on a solid support with a target-specific capture oligonucleotide probe and the hybridization of a reverse transcription primer oligonucleotide to the nucleic acid target that is joined to a third oligonucleotide. After extension of the reverse transcription primer on the target RNA and degradation of the RNA template strand with RNase H to create a priming site on the extension product, the third oligonucleotide hybridizes to the extension product and is extended to produce a double stranded DNA product. This product contains the priming and promoter sequences required for subsequent TMA amplification. The reverse transcription primer oligonucleotide and the third oligonucleotide are may be joined by a variety of polymeric linkers than may provide covalent or non-covalent linkages. The linkers may be comprised of nucleotide and/or non-nucleotide residues, and be a hybridization complex between the two oligonucleotides.

Transcription-Mediated Amplification has been used to efficiently amplify certain RNA target sequences, but the method requires careful optimization (U.S. Pat. No. 5,399,491). RNase does not fully degrade the RNA template hybridized to an RNA template, and RNase activity is sequence-dependent. Only some regions of an RNA target sequence are suitable for TMA, and the efficacy of the assay depends on the type and concentration of RNase H used with a specific sequence. These properties limit its utility, especially for highly mutliplexed assays.

The present disclosure provides a robust method for multiplex amplification of many nucleic acid targets with a process that is amenable to automation in a simple compact device for routine clinical analysis.

SUMMARY

The present disclosure is directed to methods that provide highly specific isolation and amplification of multiple nucleic acid target sequences in a sample without prior purification of nucleic acids. Universal priming sequences are introduced into copies of targets in a process that requires the use of a single solid support matrix and mild conditions for nucleic acid strand separation and recovery of the copies from the solid support. The methods can be implemented in a relatively simple device in which samples, wash solutions and reagents are introduced to a single solid support matrix from a series of reservoirs by automated fluidics.

In an embodiment, there is provided a method for the purification and replication of at least one target nucleic acid from a sample comprising:
contacting said sample with at least one oligonucleotide capture probe complementary to a sequence in said target nucleic acid;
purifying said target nucleic acid on a solid support;
hybridizing a second oligonucleotide to a nucleic acid sequence of the target nucleic acid distinct from the sequence to which the capture probe is bound to form a complex comprised of the target nucleic acid, the oligonucleotide capture probe and the second oligonucleotide;
contacting the complex with a strand displacing nucleic acid polymerase, thereby separating a duplex comprised of a newly synthesized strand and its template strand from a single-stranded nucleic acid strand complementary to the template, whereby the duplex remains attached to the solid support, and the single stranded copy is displaced from the solid support.

An embodiment disclosed herein provides a method for the purification and replication of at least one target nucleic acid from a sample, comprising:
a) contacting said sample with reverse primer/capture probe oligonucleotides having a 5' tail and incubating to anneal the reverse primer/capture probe oligonucleotides that hybridize to sequences on the target nucleic acid;
b) contacting said sample with reverse strand displacement primer oligonucleotides and incubating to anneal the reverse strand displacement primer oligonucleotides that hybridize to sequences on the target nucleic acid to form complexes of reverse primer/capture probe oligonucleotides and reverse strand displacement primer oligonucleotides bound to the target nucleic acid;
binding the complexes on a solid support by binding a ligand on the reverse primer/capture probe oligonucleotides to the solid support and washing away excess reverse primer/capture probe oligonucleotides and reverse strand displacement primer oligonucleotides and sample components other than the complexes;
extending the reverse primer/capture probe oligonucleotides with 5' tail on the target nucleic acid to form a strand, and extending the reverse strand displacement primer oligonucleotides on the target nucleic acid with a nucleic acid strand displacing polymerase, wherein extension of the reverse strand displacement primer oligonucleotides displaces, from the target nucleic acid, the extended reverse primer/capture probe oligonucleotides to give a single stranded copy, which is a copy of target nucleic acid and which is attached to the solid support;
contacting a medium containing single stranded copy with a mixture of a forward primers with a tail 5', that hybridize to sequences on the single stranded copy, and a forward strand displacement primers that hybridize to sequences on the single stranded copy, and incubating to anneal forward primers and forward strand displacement primers to single stranded copies to form complexes and wash away excess forward primers and forward strand displacement primers;
extending forward primers with tail 5' and the forward strand displacement primers on the single stranded copies immobilized on the solid support with a nucleic acid strand displacing polymerase, wherein extension of the strand displacement primers displaces the extended forward primer strands which are displaced the from the single stranded copies;

recovering the extended forward primer strands, which contain the tail 5' tail sequence of the forward primers and the complement of the 5' tail of the reverse primer capture probes, from the medium containing the solid support; and amplifying the extended forward primer strands using one or both of the attached tail 5' sequences.

In this embodiment the reverse primer/capture probe oligonucleotides and the reverse strand displacement primer oligonucleotides may be hybridized simultaneously to the target nucleic acid.

The reverse primer/capture probe oligonucleotides and the reverse strand displacement primer oligonucleotides may be hybridized separately to the target nucleic acid.

The solid support may be washed to remove any excess of the reverse strand displacement primer oligonucleotides that are not hybridized to the target nucleic acid immobilized on the solid support before contacting the complex with the nucleic acid strand displacing polymerase.

There is also disclosed a method for the purification and replication of at least one target nucleic acid from a sample, comprising: contacting said sample with a mixture of reverse primers and incubate to anneal the reverse primers to sequences in the target nucleic acid to form complexes;

binding the complexes on a solid support with capture probe/primers that hybridize to sequences on the target nucleic acid in 3' positions relative to the sequences bound by the tailed reverse primers, and wash away the excess primers and sample components other than the target sequences;

extending the reverse primers and the capture probe/primers on the target nucleic acid with a strand displacing polymerase, thereby displacing single-stranded copies of the nucleic acid target from the solid support and wherein target nucleic acid/extended capture probe/primer hybrids remain on the solid support; and adding a mixture of target-specific tailed forward primers that hybridize to sequences on the single-stranded copies and two universal primers and to the single-stranded copies of the nucleic acid targets and amplify the extension products of the target nucleic acids with a polymerase reaction.

In this embodiment the capture probe/primers hybridized to the sequence comprise the poly-adenylated sites of messenger RNA.

The capture probe/primers hybridized to the sequence comprise target-specific sequences that are different for each target nucleic acid.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Figure 1:
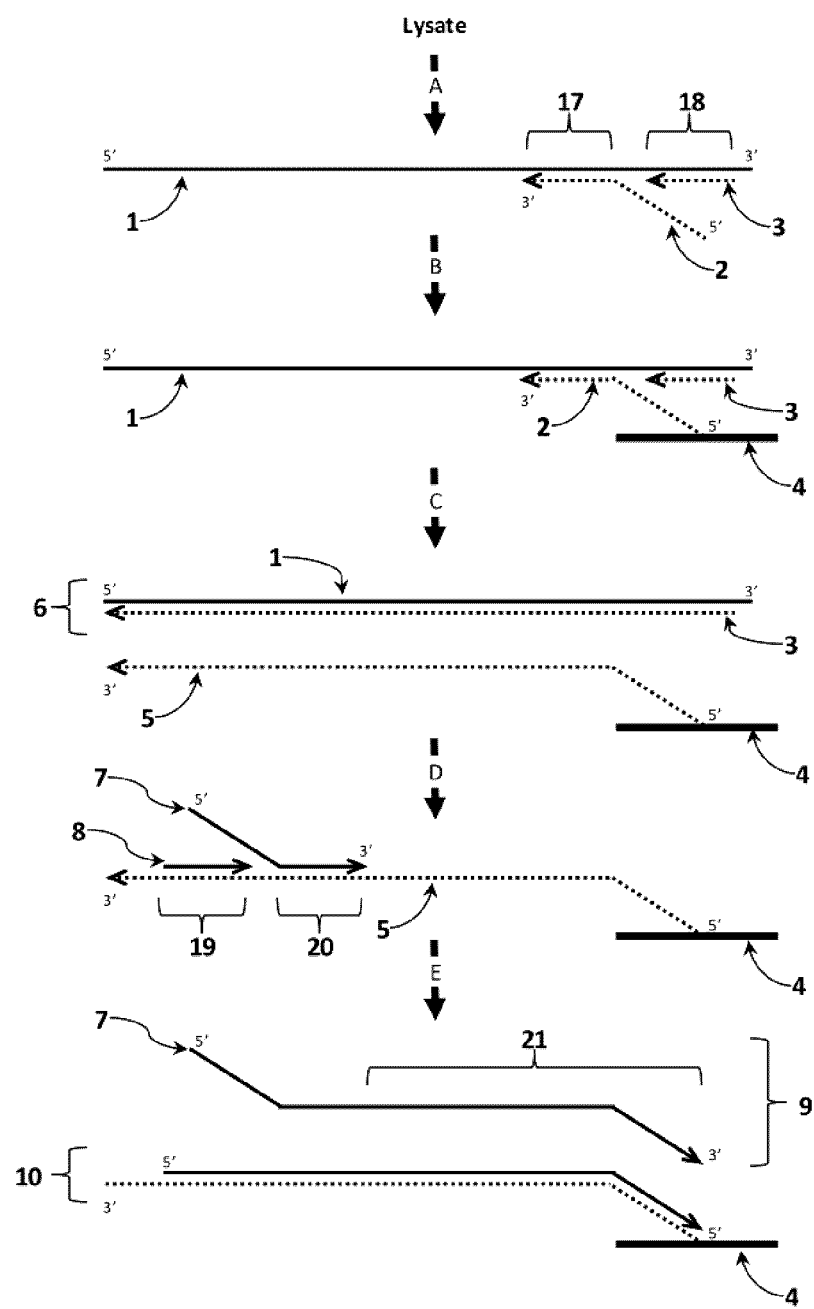
FIG. 1 is a diagram illustrating an embodiment of the present disclosure in which two strand displacement steps are utilized to produce single stranded copies of target sequences with incorporated universal priming sequences at both ends of each copy and to separate them from a solid support for subsequent processing.

Unless defined otherwise, all technical and scientific terms used herein are intended to have the same meaning as commonly understood to one of ordinary skill in the art. For example, reference to the 5' or 3' end of oligonucleotides or of 5' tails on oligonucleotides refers to the numbering of the carbon atoms on the sugar moieties making up the backbone of the polymer chains and indicate the directionality of the chains. A preferred embodiment of the present disclosure is illustrated in FIG. 1. Components of the method illustrated in are identified as follows:

(1)—Target nucleic acid to be purified and amplified
(2)—Reverse primer/capture probe oligonucleotide which is both a reverse primer and a capture probe with tail 5' which includes a ligand for immobilization
(3)—Reverse strand displacement primer oligonucleotide
(4)—Solid support with ligand binding agent
(5)—Single-stranded DNA copy immobilized on the solid support
(6)—Displaced extension product/target hybrid
(7)—Forward primer with 5' tail
(8)—Forward strand displacement primer
(9)—Displaced DNA copy with forward and reverse tail sequences
(10)—Double stranded DNA remaining bound to the solid support
(17)—A target-specific sequence on the target nucleic acid (1) to which a reverse primer/capture probe oligonucleotide (2) hybridizes
(18)—A target-specific sequence distinct from the sequence (17) and positioned in the 5' direction relative to the sequence (17) on the target nucleic acid (1). A reverse strand displacement primer oligonucleotide (3) hybridizes to this sequence.
(19)—A sequence on the single-stranded DNA copy (5) that is immobilized on the solid support (4)
(11)—A sequence on the single-stranded DNA copy (5) immobilized on the solid support (4) distinct from the sequence (19)
(12)—The extension of the forward primer (7) with tail 5' on the single-stranded DNA copy (5) which includes the complement of the sequence of the reverse primer oligonucleotide capture probe with 5' tail (2)

Steps in the method illustrated in FIG. 1 are as follows:

A. Add a mixture of two oligonucleotides (2, 3) for each target nucleic acid (1) to be purified and amplified to the sample lysate and incubate to anneal oligonucleotides (2, 3) to the target nucleic acid (1) to form complexes.

B. Capture the complexes on the solid support (4) by binding the ligand on the reverse primer (2) to solid support (4) and wash away excess oligonucleotides (2, 3) and sample components other than the target sequences. The binding of the ligand on the reverse primer (2) to the solid support (4) may occur spontaneously due to inherent affinity between the ligand on reverse primer (2) and a chemical entity previously immobilized on the solid support (4)—e.g., biotin on the oligonucleotide and streptavidin on the solid support (4). Alternatively, the reverse primer (2) may be previously attached to the solid support (4) by covalent or non-covalent means. It will be appreciated by those skilled in the art that this capture could be done either way.

C. Extend the reverse primer (2) with 5' tail on the target nucleic acid (1) to form strand (5), and extend the reverse strand displacement primer (3) on the target nucleic acid (1) with a strand displacing polymerase. The strand displacing polymerase accomplishes this due to its inherent activity. This activity is a property of certain nucleic acid polymerases that are found in nature or in polymerases engineered from them. Extension of the reverse strand displacement primer (3) displaces the extended reverse primer (2) (i.e., strand (5) which is the copy of target (1)) which is attached to the solid support (4) from the target nucleic acid (1). The double stranded extension product/target hybrid (6) is accordingly displaced from the solid support (4), and it is washed away after the polymerase reaction. The double stranded extension product/target hybrid (6) consists of the target nucleic acid (1) and the extension of oligonucleotide primer (3) on the target nucleic acid (1). One of the two strands is the target (1), and the other strand (5) is the copy of the target (1) due to the extension of primer (3).

D. Anneal the forward primer (7) with tail 5' and the forward strand displacement primer (8) to the single stranded copy of the target nucleic acid (5) immobilized on the solid support (4), and wash away the excess oligonucleotides (7, 8) after annealing.

E. Extend the forward primer (7) with 5' tail and the forward strand displacement primer (8) on the single stranded DNA copy (5) immobilized on the solid support (4) with a strand displacing polymerase. Extension of the strand displacement primer (8) displaces the extended forward primer strand (9) from the single stranded DNA copy (5). The extended forward primer strand (9), which contains the tail 5' tail sequence of the forward primer (7) and the complement of the 5' tail of the reverse primer capture probe (2), is recovered from the medium bathing the solid support (4) and can be amplified using one or both of the attached tail sequences 5'. Strand (9) is shown in FIG. 1 with a 5' tail at the left side and a 3' tail on the right side. The 3' tail on the right side is the complement of the 5' tail of the primer (2).

Thus, there is disclosed herein a method for the purification and replication of at least one target nucleic acid (1) from a sample which includes contacting the sample with at least one oligonucleotide capture probe (2) complementary to a sequence (17) in the target nucleic acid (1), purifying the target nucleic acid (1) on a solid support (4), hybridizing a second oligonucleotide (3) to a nucleic acid sequence (18) of the target nucleic acid (1) distinct from the sequence (17) to which the capture probe (2) is bound, and contacting the complex comprised of the target nucleic acid (1) and the two oligonucleotides (2, 3) with a strand displacing nucleic acid polymerase (not shown in FIG. 1), thereby separating a duplex (6) comprised of a newly synthesized strand (19) and its template strand (1) from a separate newly synthesized nucleic acid strand (5) complementary to the template (1).

The capture probe (2) and second oligonucleotide (3) may be hybridized simultaneously to the target nucleic acid (1). The solid support (4) may be washed to remove the excess of the second oligonucleotide (3) that is not hybridized to the target nucleic acid (1) captured on the solid support (4) before contacting the complex consisting of the target nucleic acid (1), the capture probe (2) and the second oligonucleotide (3) with a nucleic acid polymerase (not shown). The capture probe (2) may be extended on the target nucleic acid sequence (1), and the second oligonucleotide (3) may displace the target nucleic acid (1) from the extension product (5) of the capture probe (2), resulting in a single stranded replica (5) of the target nucleic acid (1) immobilized on the solid support (4). The capture probe (2) may include a tail sequence 5' of the target-specific sequence complementary to a sequence (17) of the target nucleic acid (1).

The second oligonucleotide (3) may displace the capture probe (2) from the target nucleic acid (1), resulting in the displacement from the solid support (4) of a double stranded hybrid (6) comprised of the target nucleic acid (1) and a replica (19) of the target (1).

In the method the third oligonucleotide (7) may be hybridized to a sequence (20) the single stranded replica (5)

of the target nucleic acid (1) and may be extended by a nucleic acid polymerase, the polymerase is not shown in FIG. 1. The solid support (4) may be washed to remove the excess of the third oligonucleotide (7) that is not hybridized to the single stranded replica (5) of the target nucleic acid (1) before contacting the complex with the nucleic acid polymerase.

The third oligonucleotide (7) may include a tail sequence 5' of the target-specific portion of the oligonucleotide which is the complement of a sequence (20) of the single stranded replica (5) of the target nucleic acid (1). In the method a fourth oligonucleotide (8) may be hybridized to a sequence (19) on the single stranded replica (5) of the target nucleic acid (1) that is distinct from the sequence (20) to which the third oligonucleotide (7) is bound, and this fourth oligonucleotide (8) can be extended by a strand displacing nucleic acid polymerase to displace a single stranded nucleic acid molecule (9) consisting of the extension product (21) of the third oligonucleotide (7) from the solid support (4).

Figure 2:
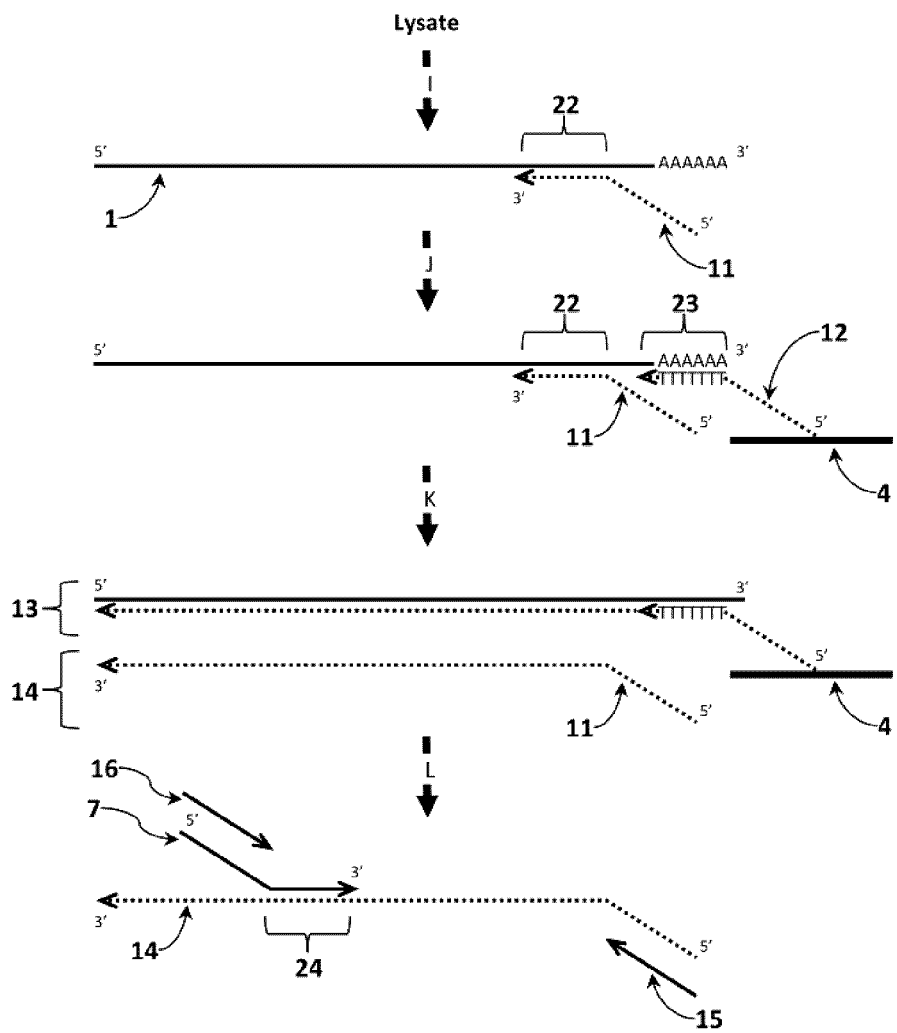
FIG. 2 is a diagram illustrating an embodiment of the present disclosure in which one strand displacement step is utilized to produce single stranded copies of target sequences with an incorporated universal priming sequence at one end of each copy and separate them from a solid support for subsequent processing.

Another embodiment is illustrated in FIG. 2. Components of the method illustrated in are identified as follows:

1—Target nucleic acid
4—Solid support
7—Forward primer with tail 5'
11—Reverse primer with tail 5'
12—Reverse primer/capture probe with its end 3' complementary to a target nucleic acid sequence and its tail end 5' capable of attaching to a solid support matrix (4). The primer/capture probe (12) in FIG. 2 has a different number than the primer/capture probe (2) in FIG. 1, since primer/capture probe (12) in FIG. 2 is positioned to the right of the tailed primer (11) and displaces the extension product of the tailed primer (11) from the solid support (4).
13—Double-stranded extension product/target hybrid retained on the solid support (4)
14—Single stranded DNA copy displaced from the solid support (4)
15—Reverse universal primer
16—Forward universal primer
22—A target-specific sequence on the target nucleic acid (1) to which a reverse primer (11) hybridizes
23—A sequence on the target nucleic acid distinct from the sequence (22) and positioned in the 3' direction relative to the target-specific sequence (22) on the target nucleic acid (1). This sequence (23) may be a sequence present on more than one target sequence in a sample, e.g., the poly-A site on eukaryotic mRNA.
24—A sequence on the single stranded DNA copy (14) displaced from the solid support (4) to which the forward primer (7) with tail 5' hybridizes Steps in the method illustrated in FIG. 2 are as follows:
I. Add a mixture of tailed reverse primers (11) to the sample containing the target (1) (one primer for each target) and anneal them to sequences (22) target nucleic acids (1).
J. Capture the complexes on the solid support (4) with capture probe/primers (12) that hybridize to sequences (23) on the targets in 3' positions relative to the sequences (22) bound by the tailed reverse primers (11), and wash away the excess primers (11) and sample components other than the target sequences (1).
K. Extend the reverse primers (11) and the capture probe/primers (12) on the target nucleic acid (1) with a strand displacing polymerase (not shown), thereby displacing single-stranded copies (14) of the nucleic acid target (1) from the solid support (4). The target nucleic acid/capture probe/primers hybrid (13) remains on the solid support (4).
L. Add a mixture of target-specific tailed forward primers (7) that hybridize to sequences (24) on the single-stranded copies (14) and two universal primers (15 and 16) to the single-stranded copies (14) of the nucleic acid targets (1) and amplify the extension products (14) of the target nucleic acids (1) with a polymerase reaction.

The forward target-specific tailed primers (7) in FIG. 2 may be present at a substantially lower concentration than the forward universal primer (16) in FIG. 2. The target-specific 5' portions of the forward tailed primers (7) in FIG. 2 may also have lower melting temperatures compared to the forward universal primer (16).

In the embodiments disclosed herein, the displaced single or double stranded replicas of the target nucleic acid sequence (1) and incorporated 5' tail sequences may be recovered in the solution bathing the solid support (4) without the use of denaturing conditions to disrupt nucleic acid hybrids.

Further, the displaced single or double stranded replicas of the target nucleic acid sequence and incorporated 5' tail sequences may be recovered in the solution bathing the solid support (4) without the use of chemical cleavage methods.

Figure 7:
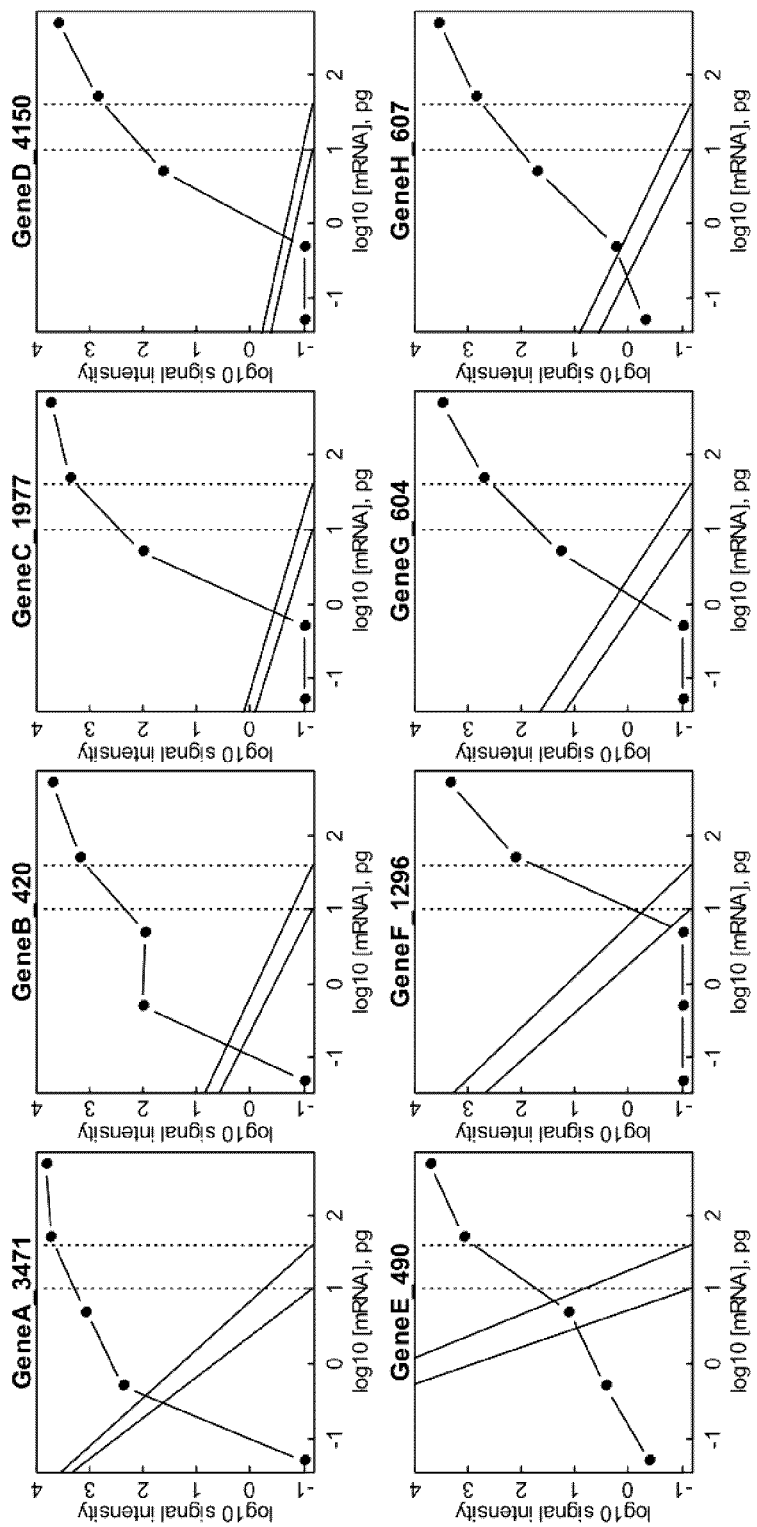
FIG. 7 presents results of an experiment in which the method disclosed herein was used to quantify small amounts (0.05 to 500 pg) of human messenger RNA from cultured breast cancer cells.

The tail 5' sequences of the forward and reverse target-specific primers (7 and 2 in FIGS. 1 and 7 and 11 in FIG. 2) may provide priming sites for subsequent amplification. This amplification may be effected with the polymerase chain reaction. Alternatively, the amplification may be effected with the strand displacement amplification reaction.

The tail sequence may provide a promoter site for subsequent amplification, and this amplification may be effected by transcription mediated amplification or NASBA.

The products of the amplification may be analyzed by a variety of methods including by hybridization on multiple different probes immobilized on a solid support such as a microarray or on different beads, by real-time PCR, or by determining the complete sequences of the products. For sequencing of the products, the 5' tails on the primers may contain adapter sequences required for subsequent sequencing reactions or tags to identify specific samples or nucleic acid targets.

The solid support (4) may be magnetic beads, a membrane or a porous flow-through chip.

The capture probe/primers (12) hybridized to the sequence (23) may comprise the poly-adenylated sites of messenger RNA. The capture probe/primers (12) hybridized to the sequence (23) comprise target-specific sequences that are different for each target nucleic acid.

In the present method nucleic acid target sequences may be isolated from crude lysates containing detergent and/or chaotropic agents, so that target nucleic acids may be isolated by the method disclosed herein without prior purification of nucleic acids.

The method in FIG. 2 is simpler than the method in FIG. 1, but the method in FIG. 1 may be more resistant to the effects of primer-dimers than the method in FIG. 2. The method in FIG. 2 requires fewer oligonucleotides for each target sequence, and it involves fewer steps than the method in FIG. 1. The forward primers in the method in FIG. 1 are hybridized to a single stranded copy of the target nucleic acid while it is immobilized on the solid support, so that the excess forward primers can be washed away before the subsequent polymerase reaction. The forward primers in the method in FIG. 2 are hybridized to the a single stranded copy of the target nucleic acid after it has been displaced from the solid support, so that the excess primers cannot be washed away. In this case primer-dimers may form between different gene-specific forward primers. However, the formation of these primer-dimer artifacts will be limited by minimizing their concentration. Furthermore, their amplification will be limited because all of the primer-dimers formed from the forward gene-specific primers will have the same tail sequence on their 5' ends and the complement of the 5' tail sequence on their 3' ends, so they will form hairpin structures and will not be efficiently amplified.

A kit may be produced comprising reagents for performing the present method.

EXAMPLES

The method outlined in FIG. 1 was tested with different types of samples including synthetic RNAs (arbitrary random and HIV sequences) and total RNA from breast cancer cells and whole blood. The method of the present disclosure outlined in FIG. 2 was tested with total RNA from breast cancer cells.

Synthetic RNA (Arbitrary Random Sequences & HIV 5'LTR Sequence)

Figure 3:
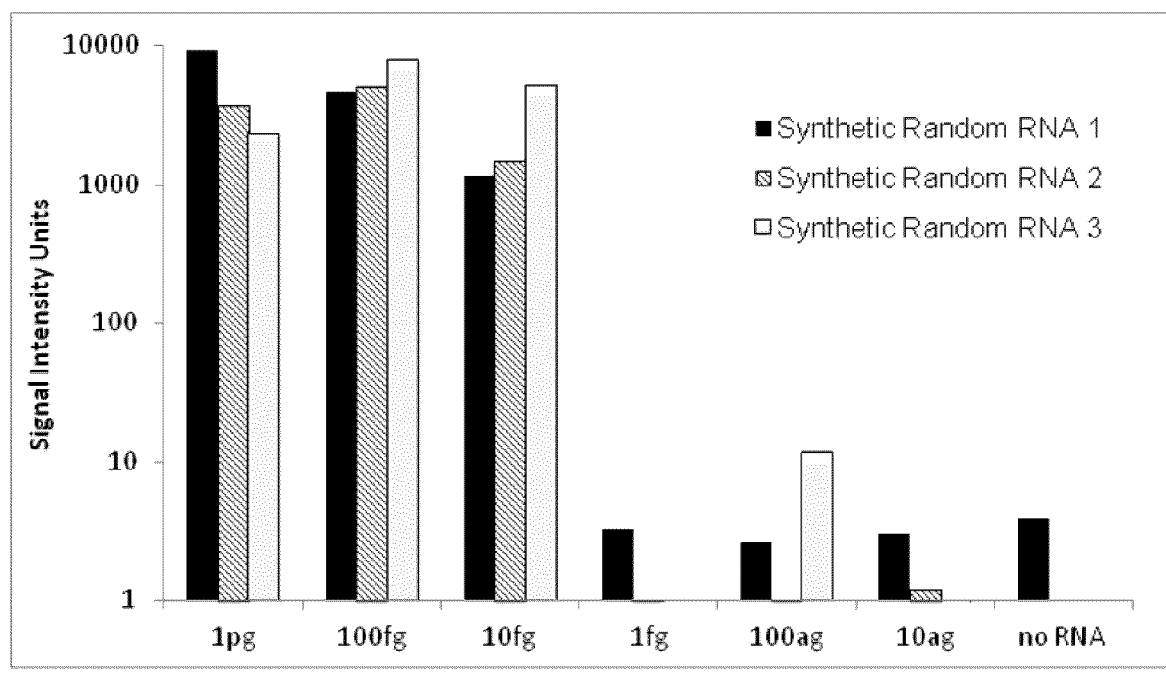
FIG. 3 presents results of an experiment in which the method disclosed herein was used to detect small quantities of three synthetic RNA molecules.

The method outlined in FIG. 1 was tested with synthetic RNA targets. A pool of three different synthetic RNA targets (~400 bases each) were spiked into detergent-containing lysis/hybridization buffer and their respective strand displacement primers and biotinylated capture probes containing a universal sequence at the 5' end were allowed to anneal. The complexes were captured on streptavidin magnetic beads and excess probes and primers were washed away before reverse transcription/strand displacement reaction. After reverse transcription the displaced double stranded RNA:cDNA complexes were washed away, and a second set of primers was added to the extension product of the capture probe to introduce another universal sequence at the 5' end by a second strand displacement reaction. The supernatant was added to a PCR mix containing universal forward primers and biotinylated universal reverse primers, and the targets were amplified. The biotinylated PCR products were hybridized on flow-through oligonucleotide microarrays (Quinn et al, J Transl Med. 7:55, 2009), followed by washes, incubation with streptavidin-HRP and further washes. The presence of targets was detected by chemiluminescence. Signals were detected down to 10 femtograms (fg) of for all three synthetic RNA targets that were spiked into the same lysis/hybridization buffer (FIG. 3).

Figure 4:
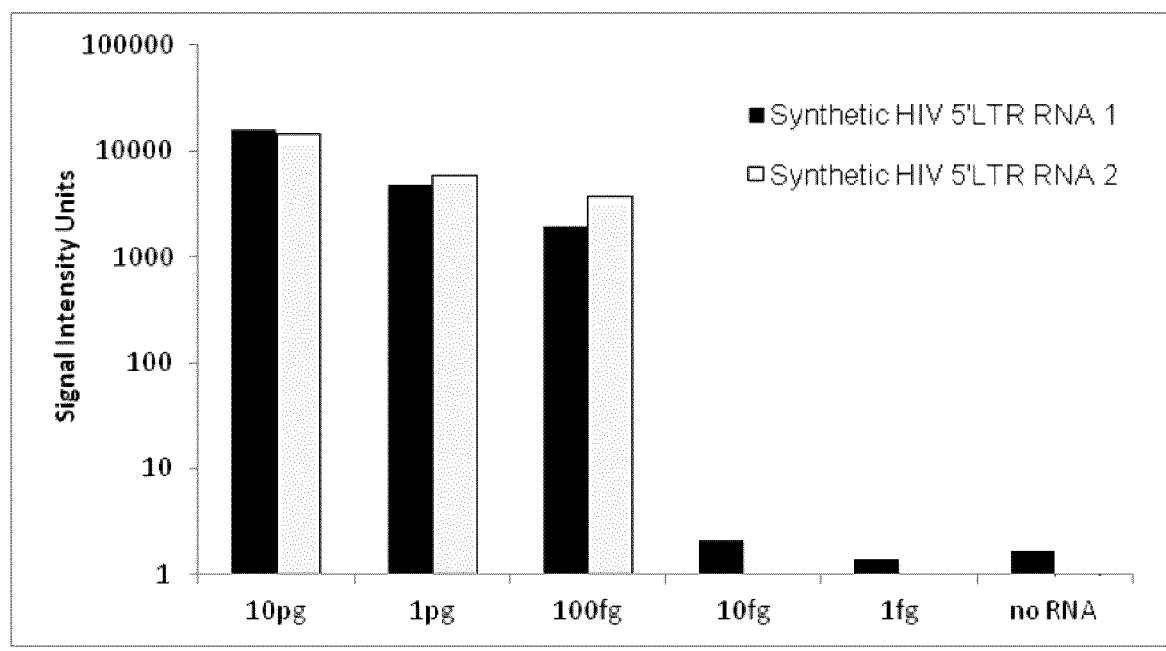
FIG. 4 presents results of an experiment in which the method disclosed herein was used to detect small quantities of HIV RNA.

Similarly, synthetic RNA with HIV 5'LTR sequence (~600 bases) was used to test the method outlined in FIG. 1. In this experiment, two different sets of biotinylated capture probes and primers targeting two different regions of the HIV sequence were hybridized to the synthetic HIV RNA and processed using the aforementioned method. Signals were detected down to 100 fg for synthetic HIV RNA targets spiked into lysis/hybridization method (FIG. 4).

SKBR3 Breast Cancer Cell Line and Universal Human Reference Total RNA

Total RNA derived from mammalian SKBR3 breast cancer cell line was used to test the feasibility of multiple target detection with the present method. Universal Human Reference (UHR) total RNA, comprised of RNA derived from 10 different cell lines, was used as control. Several relevant genes associated with breast cancer (ERBB2, EPCAM, KRT9, CCND1) and a housekeeping gene ACTG1 were selected as mRNA targets. Biotinylated capture probes and primers were designed for each of these targets and samples were spiked into detergent-containing lysis/hybridization buffer and processed using method outlined in FIG. 1.

Figure 5:
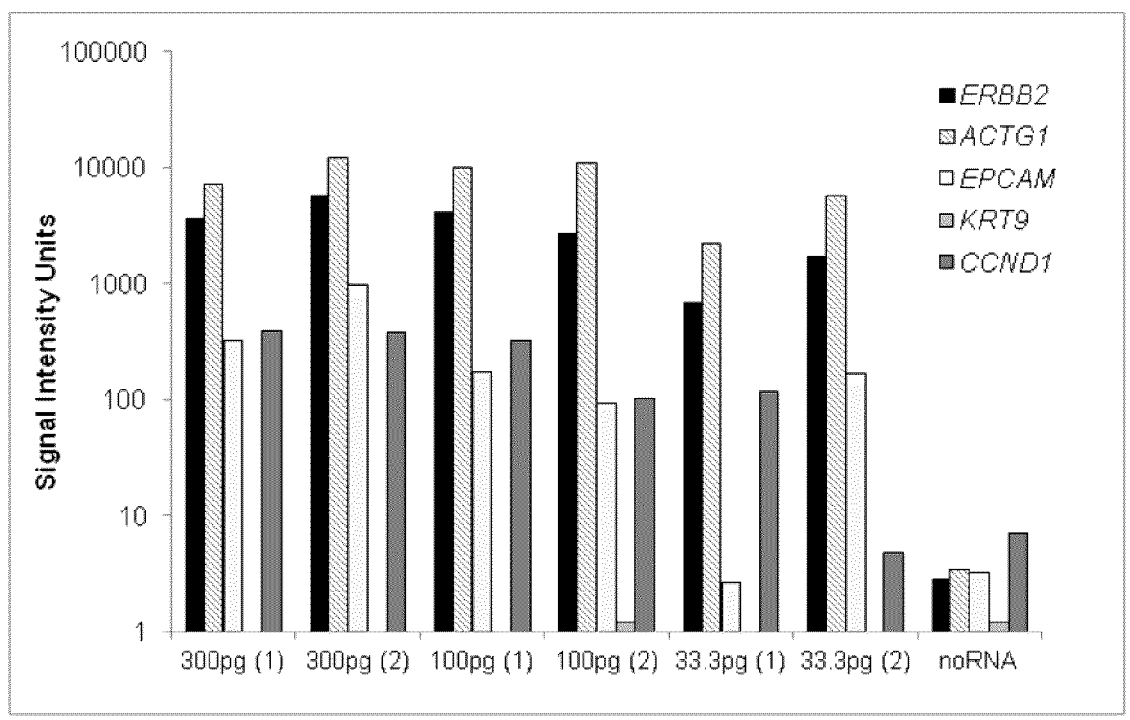
FIG. 5 presents results of an experiment in which the method disclosed herein was used to detect small amounts (33 to 300 pg) of human messenger RNA from cultured breast cancer cells.

Different amounts of total RNA from SKBR3 breast cancer cells were tested and signals were detected down to 33.3 pg for housekeeping gene ACTG1 and a subset of the breast cancer genes (FIG. 5). KRT9 was not detected in any of the samples as it is not expressed in this cell line. The housekeeping gene ACTG1 was detected down to 5 pg of UHR total RNA, but none of the breast cancer genes were detected, presumably because they were not expressed in any of the cell lines used to generate this sample.

SKBR3 Breast Cancer Cells Spiked into Blood

To test the feasibility of measuring levels of mRNA in small numbers of tumour cells harvested from blood, 10 or 100 cells of SKBR3 breast cancer cells were spiked into 10 mL of blood, and tumor cells were harvested from the blood with a device that partially purified tumor cells from blood cells on the basis of the physical characteristics of the cells. Total RNA from the cells were then processed as described above (as outlined in FIG. 1). The harvested cells were predominantly white blood cells, and in some cases only RNA from white blood cells was used as control.

Figure 6:
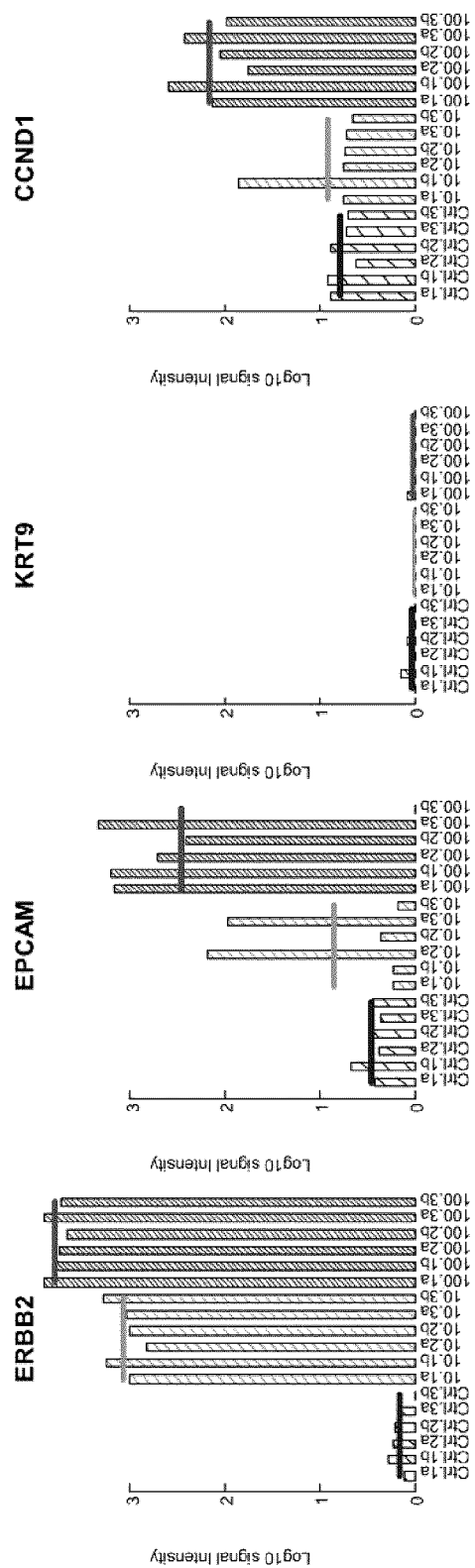
FIG. 6 presents results of an experiment in which the method disclosed herein was used to detect messenger RNA from small numbers of breast cancer cells isolated from blood. Specifically, signal intensities for four genes, using log10 scale. Six replicates of three sample types: control harvested blood cells (least dense hatching), harvested blood cells with 10 SKBR3 cells (more dense hatching) and harvested blood cells with 100 SKBR3 cells (most dense hatching). The solid bars indicate the means of replicates.

Six replicates of each sample were tested: blood with no tumor cells, 10 mL of blood with 10 tumor cells, and 10 mL of blood with 100 tumor cells (arranged left to right in each bar plot in FIG. 6). In addition to housekeeping genes, mRNA transcripts of three different genes (ERBB2, EPCAM and CCND1) were detected unambiguously when 100 tumor cells had been spiked into 10 mL of blood. The transcript of the ERBB2 gene was detected when only 10 cells had been spiked into 10 mL of blood at a level about ten-fold lower than when 100 tumor cells had been spiked into the blood. The ERBB2 gene is known to be expressed at a relatively high level in SKBR3 cells.

mRNA Quantification from SKBR3 Breast Cancer cells

The method outlined in FIG. 2 was used to capture mRNA from small amounts of total RNA from SKBR3 cancer cells and to amplify and quantify specific genes using flow-through oligonucleotide microarrays. Three different regions of each of eight target genes were simultaneously amplified and quantified using oligonucleotide probe sets specific to each region of the genes. The object of this 24-plex test was to screen different oligonucleotide probe sets to discover those that provided the greatest sensitivity. The results for one probe set for each of the eight genes are presented in FIG. 7. The signal intensities depended on the amount of total RNA used in the assay. Some gene transcripts were detectable in only 1 picogram (pg) of total RNA (zero on the axis of the log10 plot). The dotted vertical lines indicate the range of total RNA expected from single mammalian cells (see Roozemond, *Histochem J.* 8:625, 1976; Uemura, *Brain Res Bull* 5, 117, 1980; Brady, *Yeast* 17:211, 2000). The results indicate that the method of the this disclosure will enable assessment of the expression levels of multiple mRNA transcripts in single cells.

Therefore what is claimed is:

1. A method for the purification and replication of target nucleic acids (1) from a sample, comprising:
    a) contacting said sample with a mixture of tailed reverse primers (11) in a buffer solution and incubating to anneal the reverse primers (11) with 5' tail sequences to sequences (22) in the target nucleic acids (1) to form soluble complexes;
    b) binding the formed soluble complexes on a solid support (4) with capture probe/primers (12) that hybridize to sequences (23) on the target nucleic acids (1) in 3' positions relative to the sequences (22) bound by the tailed reverse primers (11), wherein steps a) and b) are performed in no specific order;

c) washing away excess tailed primers (11) and sample components other than the target nucleic acids (1);

d) after washing away excess tailed primers (11) and sample components other than the target nucleic acids (1), extending the tailed reverse primers (11) and the capture probe/primers (12) on the target nucleic acids (1) with a strand displacing polymerase, thereby displacing single-stranded copies (14) of the target nucleic acids (1) with 5' tail sequences from the solid support (4) and wherein target nucleic acids/extended capture probe/primer hybrids (13) remain on the solid support 4;

e) adding a mixture of target-specific tailed forward primers (7) that hybridize to sequences (24) on the single-stranded copies (14) that were displaced from the solid support (4) and copying the single-stranded copies (14) of the target nucleic acids (1) with a polymerase reaction to form complements of the single-stranded copies (14) containing the 5' tails of the target-specific tailed forward primers at their 5' end and the complements of the 5' tails of the reverse primers at their 3' ends; and f) amplifying said formed complements of the single-stranded copies by priming synthesis with universal primers (15 and 16) capable of priming synthesis at the 5' tails of the complements of the single-stranded copies (14) or of complements thereof.

2. The method according to claim 1 wherein the target nucleic acids (1) are messenger RNA molecules, and the capture probe/primers (12) are hybridized to poly-adenylated sites of the messenger RNA molecules.

3. The method according to claim 1 wherein the capture probe/primers (12) hybridized to the sequences (23) on the target nucleic acids (1) comprise target-specific sequences that are different for each of the target nucleic acids (1).

4. The method according to claim 1 wherein the capture probe/primers (12) and reverse primers (11) are hybridized simultaneously to the target nucleic acids (1).

5. The method according to claim 1 wherein the capture probe/primers (12) and reverse primers (11) are hybridized separately to the target nucleic acids (1).

6. A method for the purification and replication of target nucleic acids (1) from a sample comprising:

contacting said sample with oligonucleotide capture probe/primers (12) complementary to sequences (23) in said target nucleic acids (1);

purifying said target nucleic acids (1) on a solid support (4);

hybridizing tailed reverse primers (11) to nucleic acid sequences (22) of the target nucleic acids (1) distinct from the sequences (23) to which the oligonucleotide capture probe/primers (12) are bound and in positions (22) 5' on the target nucleic acids (1) relative to the oligonucleotide capture probe/primers (12) to form complexes comprised of the target nucleic acids (1), the oligonucleotide capture probe/primers (12) and the tailed reverse primers (11);

contacting the complexes with a strand displacing nucleic acid polymerase, thereby separating duplexes (13) comprised of copies of the target nucleic acids (1) hybridized to the target nucleic acids (1) from single-stranded nucleic acid copies (14) of the target nucleic acids (1), whereby the duplexes (13) remain attached to the solid support (4), and the single-stranded nucleic acid copies (14) are displaced from the solid support (4).

7. The method according to claim 6 in which the oligonucleotide capture probe/primers (12) and the tailed reverse primers (11) are hybridized simultaneously to the target nucleic acids (1).

8. The method according to claim 6 in which the oligonucleotide capture probe/primers (12) and the tailed reverse primers (11) are hybridized separately to the target nucleic acids (1).

9. The method according to claim 6 in which the solid support (4) is washed to remove the excess of the tailed reverse primers (11) that are not hybridized to the target nucleic acids (1) captured on the solid support (4) before contacting the complex with a nucleic acid polymerase.

10. The method according to claim 6 in which the capture probe/primers (12) displace the tailed reverse primers (11) from the target nucleic acids (1), resulting in the displacement from the solid support (4) of single-stranded copies (14) of the target nucleic acids (1) with the tailed reverse primers (11) at the 5' ends.

11. The method according to claim 10 in which the tails of the tailed reverse primers (11) are 5' of the target-specific portion of the tailed reverse primers (11).

12. The method according to claim 10 in which the tail sequences of the tailed reverse primers (11) provide priming sites for subsequent amplification.

13. The method according to claim 12 in which amplification is effected with the polymerase chain reaction.

14. The method according to claim 12 in which amplification is effected with the strand displacement amplification reaction.

15. The method according to claim 11 in which the tail sequences of the tailed reverse primers (11) provide a promoter site for subsequent amplification.

16. The method according to claim 15 in which amplification is effected by transcription mediated amplification or NASBA.

17. The method according to claim 6 in which the solid support (4) is a flow-through chip.

18. The method according to claim 10 in which the displaced single-stranded copies (14) are recovered in the solution bathing the solid support (4) without the use of denaturing conditions to disrupt nucleic acid hybrids.

19. The method according to claim 10 which the displaced single-stranded copies (14) are recovered in the solution bathing the solid support (4) without the use of chemical cleavage methods.

20. The method according to claim 6 in which the target nucleic acids (1) are isolated from crude lysates containing detergent and/or chaotropic agents.

21. A method according to 6 in which products of amplification are analyzed by hybridization to probes immobilized on a solid support.

22. A method according to claim 6 in which products of amplification are analyzed by hybridization to probes immobilized on a population of beads.

23. A method according to claim 6 in which products of amplification are analyzed by PCR amplification.

24. A method according to claim 6 in which products of amplification are analyzed by determining a sequence of the amplification products.

25. A method according to claim 24 in which the tail sequences of the tailed reverse primers (11) contain adapter sequences required for subsequent sequencing reactions or tags to identify specific samples or nucleic acid targets.

26. The method according to claim 1 wherein the complements of the single-stranded copies (14) are amplified with the polymerase chain reaction using two universal primers.

27. A method according to claim 1 in which products of amplification are analyzed by hybridization to probes immobilized on a solid support.

28. A method according to claim 1 in which products of amplification are analyzed by hybridization to probes immobilized on a population of beads.

29. A method according to claim 1 in which products of amplification are analyzed by PCR amplification.

30. A method according to claim 1 in which of amplification are analyzed by determining a sequence of the amplification products.

31. A method according to claim 30 in which the tail sequences of the tailed reverse primers (11) contain adapter sequences required for subsequent sequencing reactions or tags to identify specific samples or nucleic acid targets.

* * * * *